United States Patent [19]

Meyer et al.

[11] Patent Number: 5,678,579
[45] Date of Patent: *Oct. 21, 1997

[54] APPARATUS AND METHOD FOR POSITIONING AND MOVING A FLEXIBLE ELEMENT

[75] Inventors: Stuart L. Meyer, Chicago, Ill.; Jonathan I. Meyer, Shaker-Heights, Ohio; Eric S. Meyer, Gaithersburg, Md.; David M. Meyer, Stanford, Calif.

[73] Assignee: Televideo Consultants, Inc., Evanston, Ill.

[*] Notice: The term of this patent shall not extend beyond the expiration date of Pat. No. 5,469,874.

[21] Appl. No.: 387,350

[22] Filed: Feb. 13, 1995

Related U.S. Application Data

[63] Continuation-in-part of Ser. No. 201,344, Feb. 24, 1994, Pat. No. 5,469,874.
[51] Int. Cl.⁶ ............................................. A61C 15/00
[52] U.S. Cl. ..................... 132/323; 132/324; 132/325; 132/326; 132/327; 600/104
[58] Field of Search .................... 132/323, 324, 132/325, 326, 327; 606/113, 137; 600/104

[56] References Cited

U.S. PATENT DOCUMENTS

| | | | |
|---|---|---|---|
| 3,799,177 | 3/1974 | Bragg | 132/326 |
| 4,982,752 | 1/1991 | Rodriguez | 132/324 |
| 5,123,432 | 6/1992 | Wyss | 132/323 |
| 5,224,501 | 7/1993 | McKenzie | 132/323 |
| 5,327,977 | 7/1994 | Lukashuk | 132/324 |
| 5,535,759 | 7/1996 | Wilk | 606/113 |

*Primary Examiner*—Gene Mancene
*Assistant Examiner*—Philogene Pedro
*Attorney, Agent, or Firm*—Brinks Hofer Gilson & Lione; Richard G. Lione; Michael P. Chu

[57] ABSTRACT

An apparatus and method for positioning and moving a flexible element in space. The element is formed into a loop mounted on a pair of positioning handles. The loop, which may be a real or a virtual loop, is mounted on the two handles so as to be movable relative to the handles and to form a working segment of the element between corresponding one free end of the handles, each by one hand or both by the fingers (and thumb) of one hand, positions the working segment in space and manipulation of the loop moves the working segment relative to the handles. The apparatus and method find advantageous application in dental flossing devices, a laparoscopic surgical device or cutting or abrading devices, for example.

28 Claims, 7 Drawing Sheets

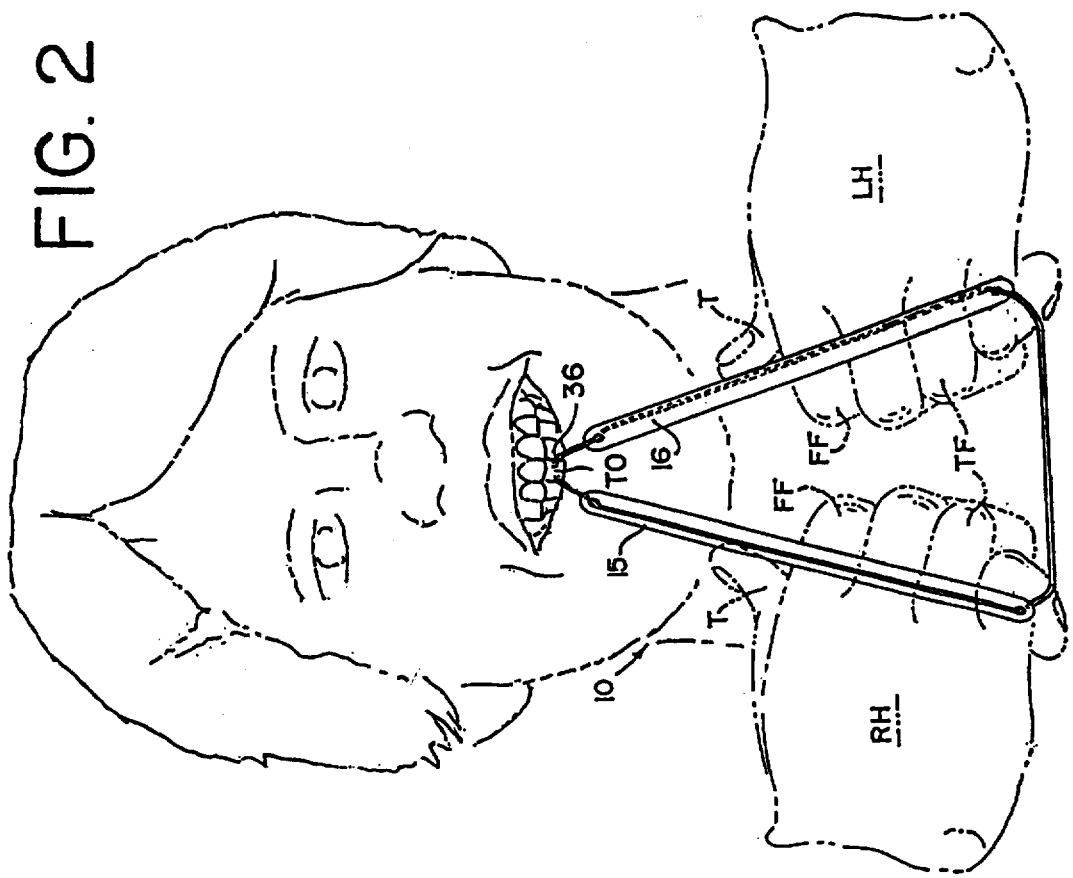
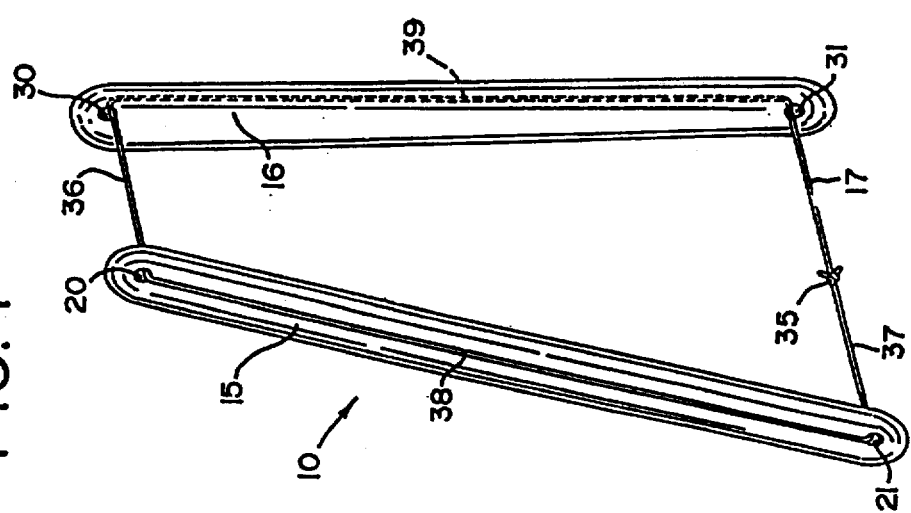

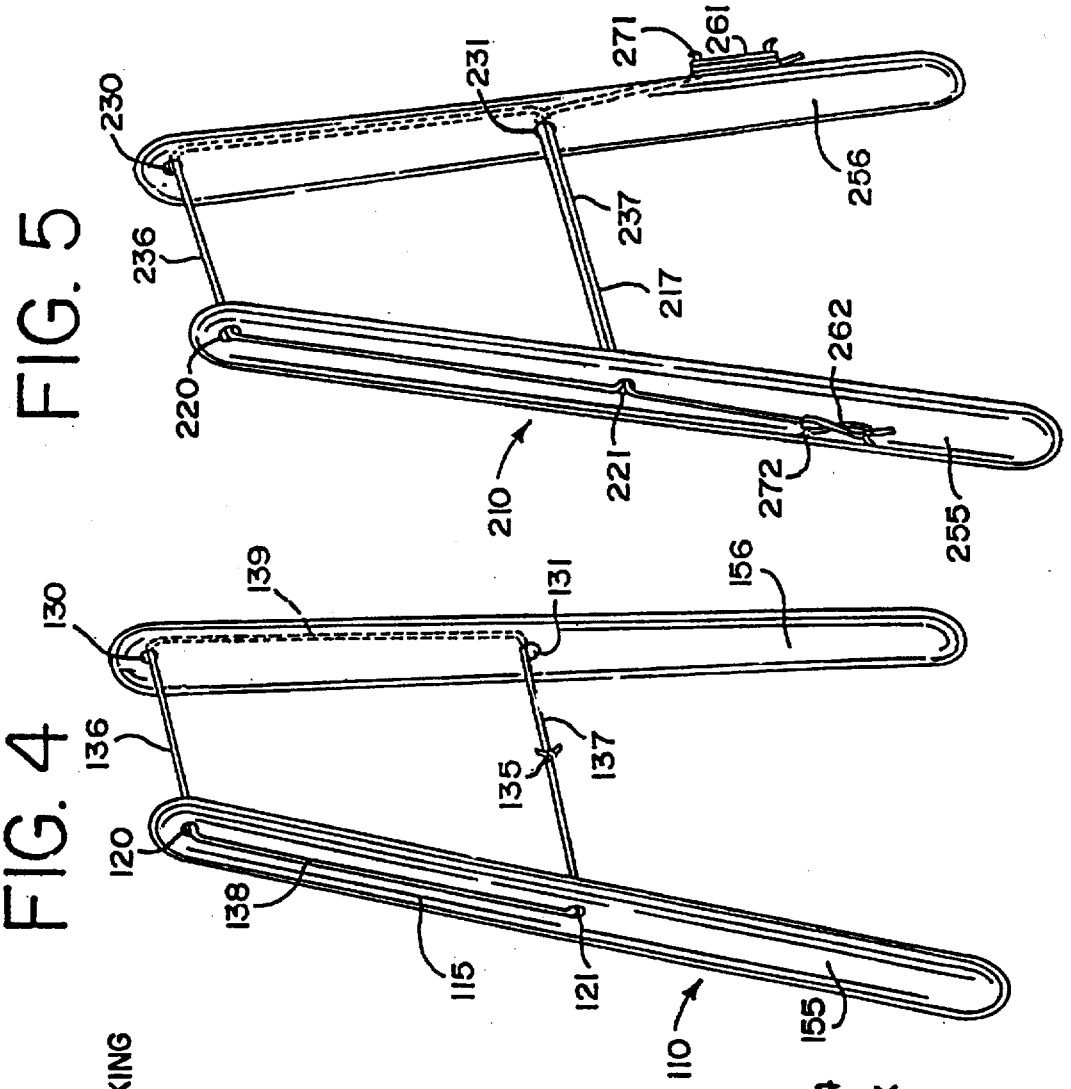

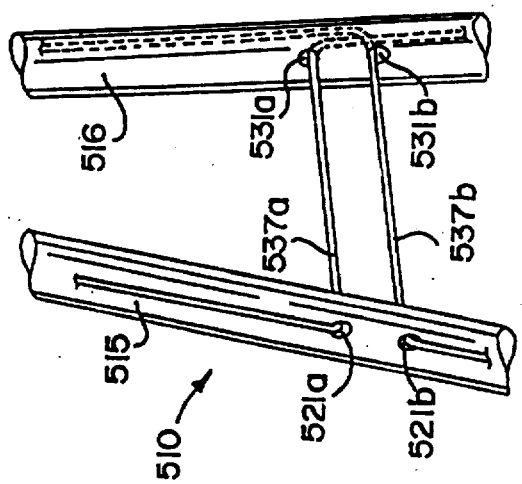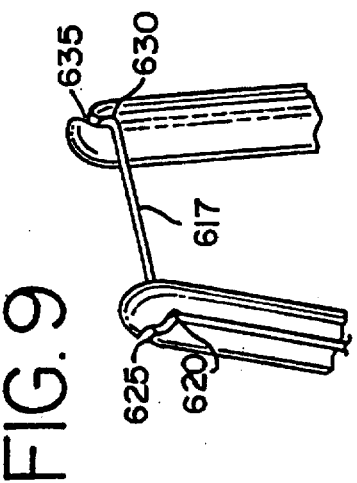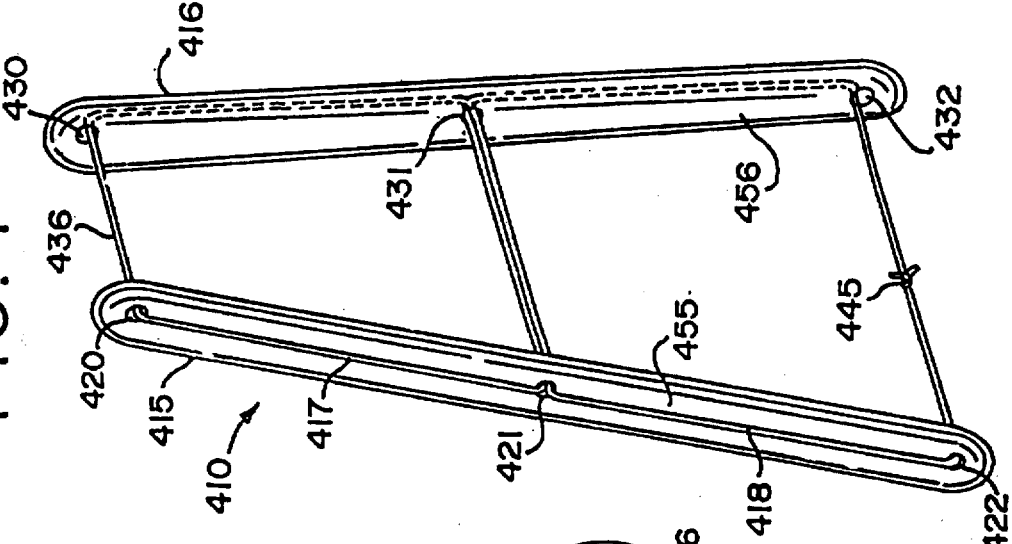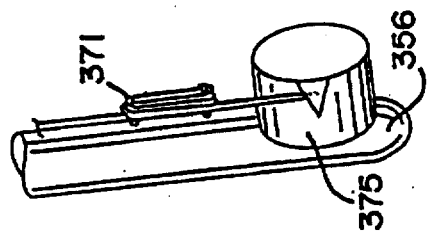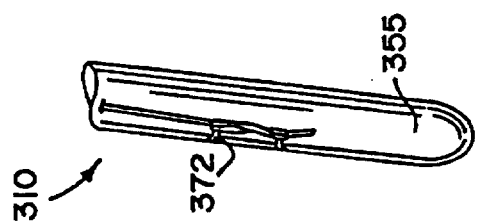

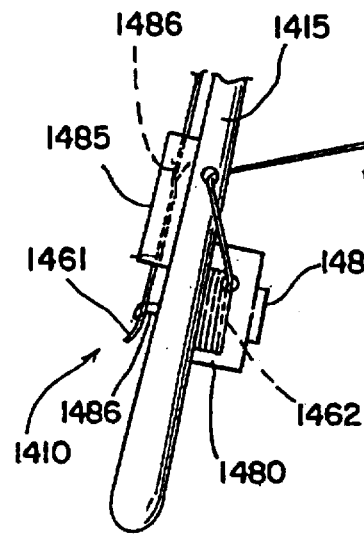
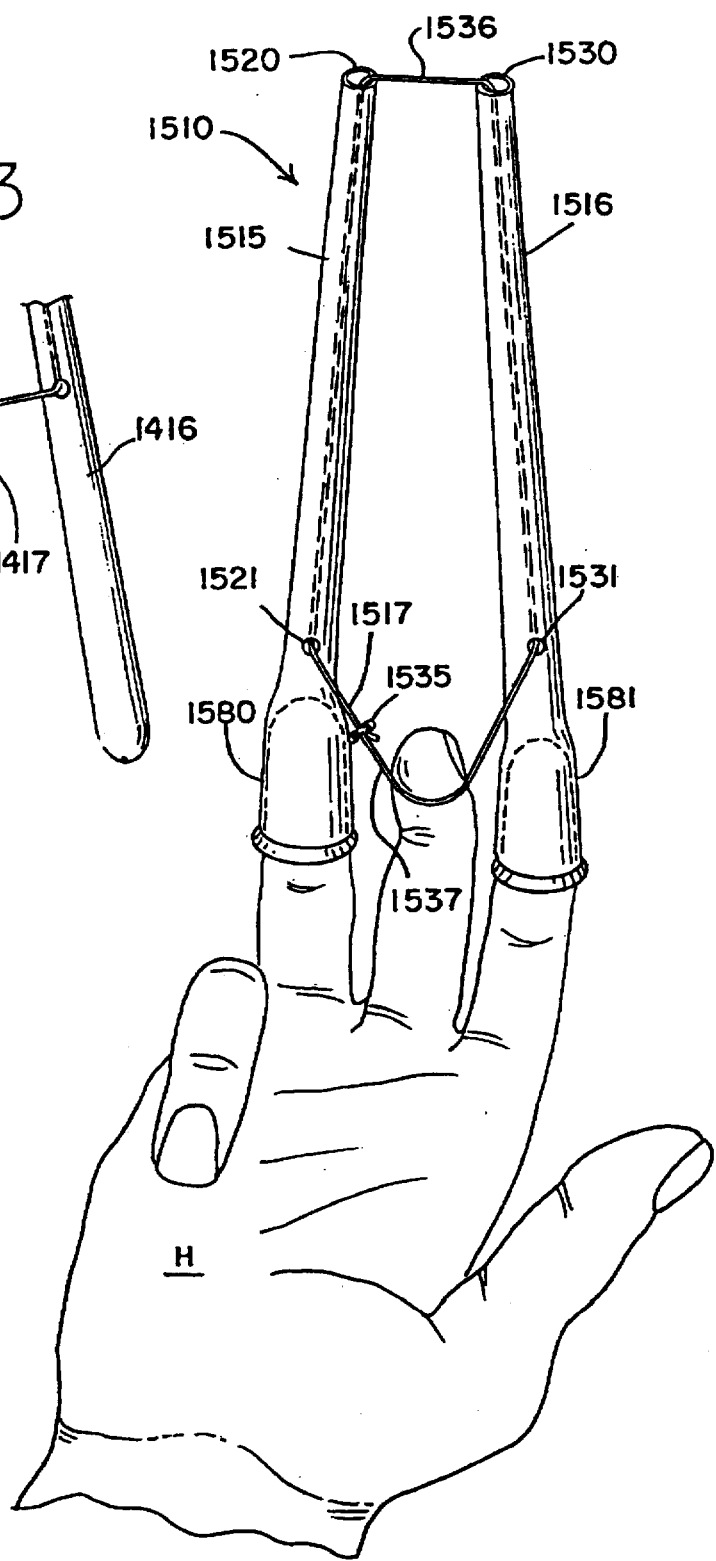

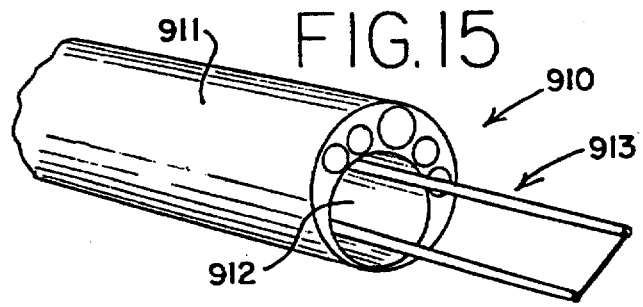
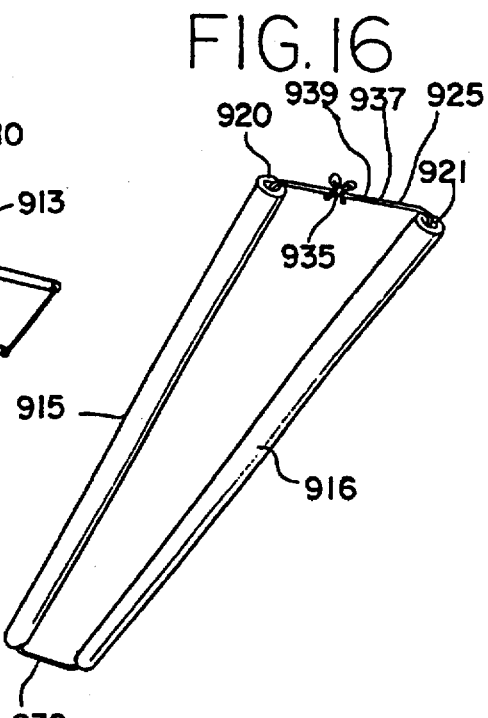
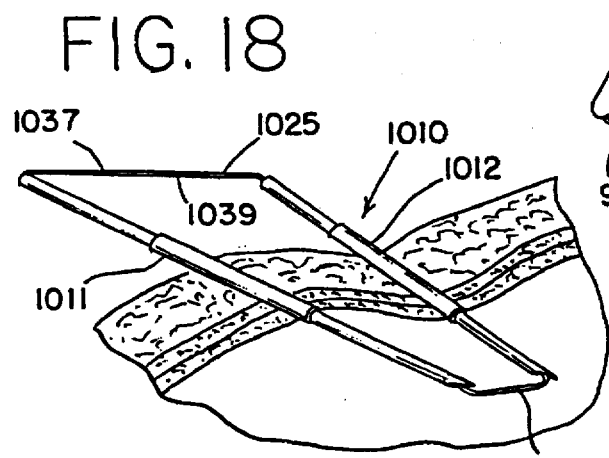
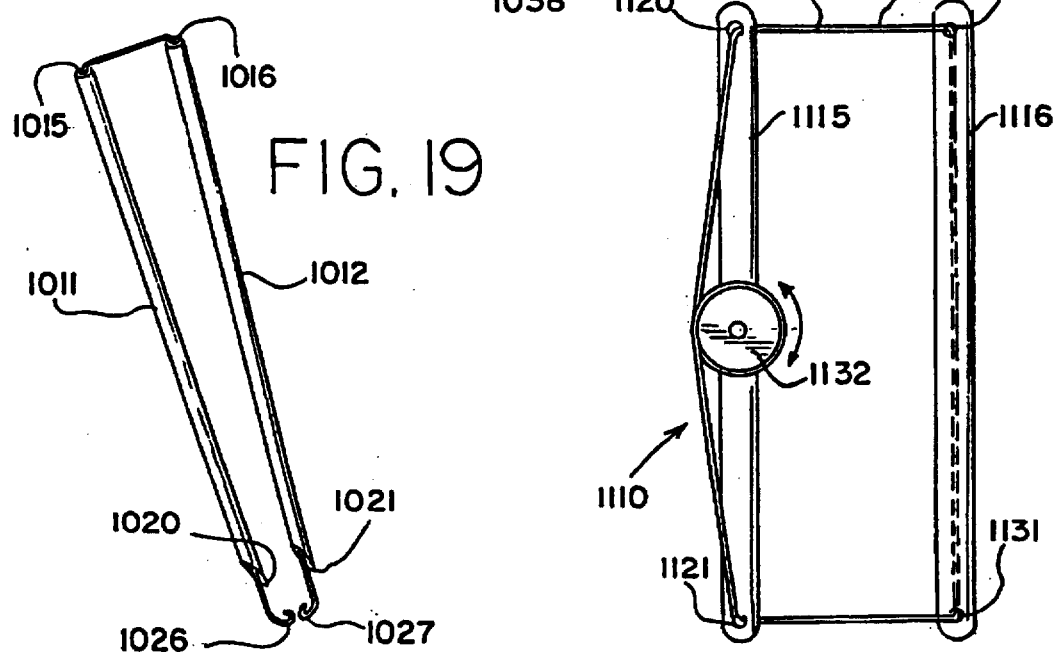

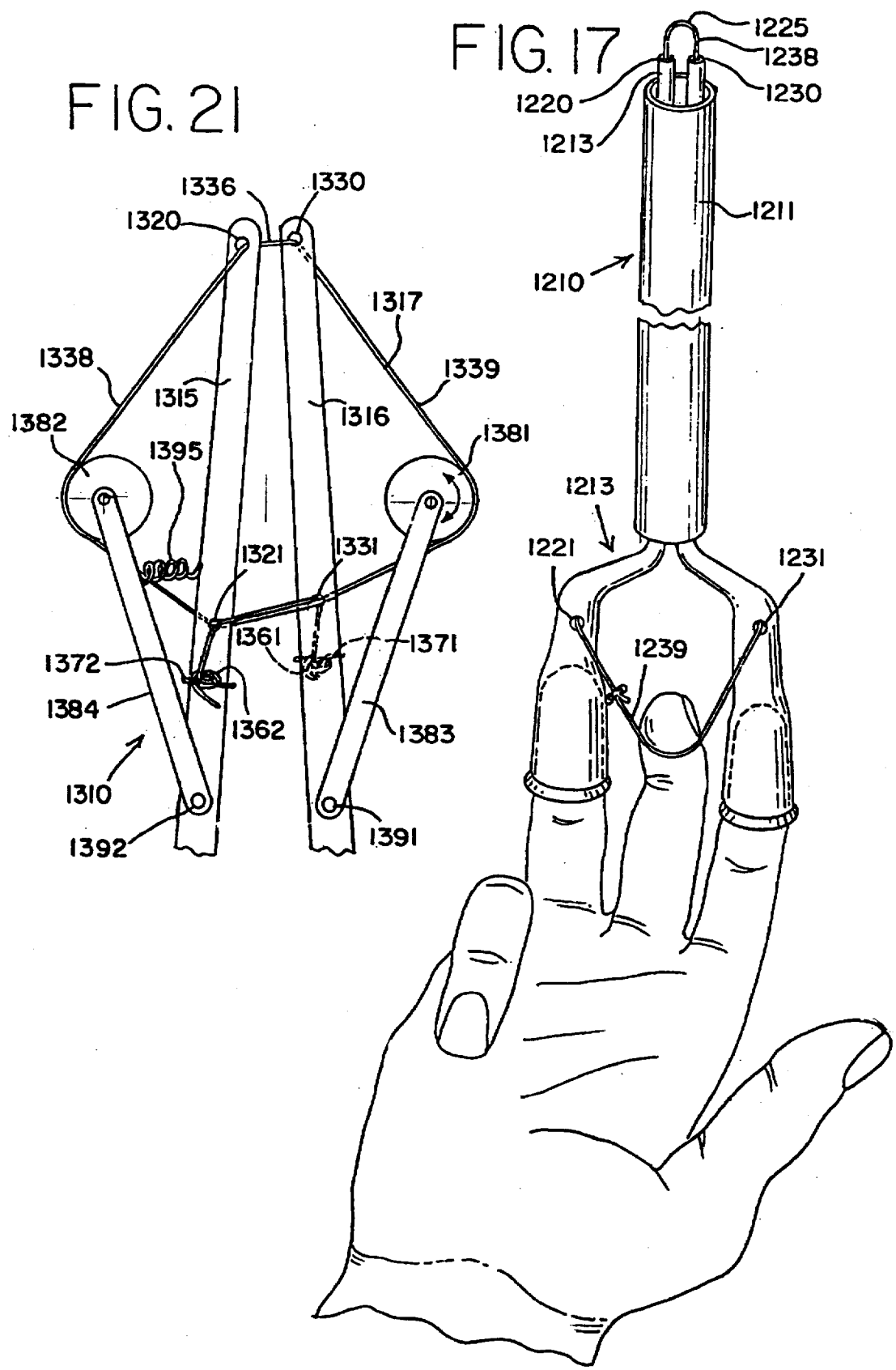

APPARATUS AND METHOD FOR POSITIONING AND MOVING A FLEXIBLE ELEMENT

RELATED APPLICATION

This application is a continuation-in-part of U.S. application Ser. No. 08/201,344, filed Feb. 24, 1994, entitled APPARATUS AND METHOD FOR PERFORMING DENTAL FLOSSING, now U.S. Pat. No. 5,469,874.

FIELD OF THE INVENTION

This invention relates generally to an apparatus and method for positioning and moving a flexible element, e.g., a cord, wire or band, in space to use the element for performing various tasks. The tasks might be as diverse as dental flossing, laparoscopic surgery or mechanical sanding or abrading.

BACKGROUND OF THE INVENTION

It has long been known in the field of dental hygiene, for example, that it is important to remove food particles, tartar, and plaque from the teeth at least once a day. The removal of such dental contaminants may be accomplished by various means such as by brushing, water spray or the use of dental floss.

Dental floss is conventionally held in the hands and manipulated by the fingers. The floss is inserted between two adjacent teeth, or looped partially around a single tooth and pulled, or pushed back and forth against the tooth to remove the food particles, tartar and plaque. This procedure requires a certain amount of manual dexterity and also requires the flosser to insert his or her fingers into the mouth.

A variety of mechanical devices have been developed to aid in the use of dental floss. Among these are devices consisting of a forked or U-shaped handle. In these devices a length of dental floss is tautly stretched between the two tines of a device. The device is manipulated from outside the mouth so as to draw the dental floss up and down against the surface of the tooth to be cleaned. Examples of such devices are found in Schiff U.S. Pat. No. Des 251,074 and the Yafai U.S. Pat. No. 4,304,246. In the latter, the floss is in the form of a loop which is stretched around the device.

In another flossing device, illustrated and described in the Wyss U.S. Pat. No. 5,123,432, parallel handles have a floss loop extending through them and interconnected across opposite ends. The handles are spaced at their mid-points by a spacer member which forms a fulcrum. The handles are manipulated by squeezing them at one end so that they pivot in a plane about the fulcrum and draw the floss tight at one end (the flossing end). In lieu of the spacer member illustrated, the handles may be manipulated in the same manner about a fulcrum formed by the flosser's finger.

In yet another flossing device, illustrated and described in the Bragg U.S. Pat. No. 3,799,177, the use of two separate handles is shown. A length of floss is stretched between the corresponding working ends of the handles and flossing accomplished by manipulating the other ends separately.

SUMMARY OF THE INVENTION

An object of the invention is to provide a new and improved apparatus for positioning and moving a flexible element in space to use the element for performing various tasks.

Another object is to provide an improved apparatus for dental flossing.

Still another object is to provide an improved flossing apparatus comprising a pair of independently controlled flossing handles which are interconnected only by a loop of floss.

Yet another object is to provide an improved dental flossing apparatus wherein segments of the floss loop which interconnect the handles are lengthened and shortened at will and in an endless variety of ways by manipulating the handles independently of each other.

Another object is to provide a flossing apparatus which can be effectively used while inserting only a minimal amount of the apparatus into the mouth.

Still another object is to provide a flossing apparatus which can readily be adapted to incorporate a lengthy store of floss.

A further object provides a flossing apparatus which is simple and inexpensive to manufacture.

Another object is to provide an improved apparatus for performing laparoscopic surgery.

Another object is to provide an improved apparatus for performing mechanical sawing or abrading.

Yet an additional object is to provide a new and improved method of positioning and moving a flexible element in space to accomplish various practical work and perform desired tasks.

Another object of the present invention is to provide a new and improved method of dental flossing.

Various of the foregoing and other objects are realized in accord with one aspect of the present invention by providing a flossing apparatus comprising a pair of separate and distinct flossing handles which are interconnected by a loop of dental floss. The loop is formed from a length of dental floss and includes a working segment of floss which interconnects corresponding free ends of the handles, a control segment which interconnects the handles at points displaced from the free ends, and a pair of side segments which run along corresponding handles between respective ends of the working and control segments. The handles are free to move on all axes relative to each other, restrained only by the dimensions of the loop. They are also free to move relative to the loop.

In one embodiment of the flossing apparatus, the handles are of identical length. The floss loop passes through connecting apertures at opposite ends of each handle. Free ends of the length of floss which form the loop are tied together or otherwise interconnected in the control segment (or side segments) of the loop.

In another embodiment of the flossing apparatus, the handles are of identical length but are considerably longer than those in the previously described embodiment. The handles each extend beyond the point where the control segment of the floss loop interconnects with handles, providing handle extensions, if you will.

In a modification of the other embodiment, the single, continuous loop is replaced by a floss store mounted on one of the handle extensions. A loop is then effectively formed between the handles by passing it through the connecting apertures twice to form a control segment—in a manner hereinafter explained. The floss is then anchored adjacent the floss store, and the free end of the floss is anchored to the other handle extension.

In this modification, a variety of floss storing, cutting and anchoring mechanisms may be employed. For example, the floss store may be simply formed around a cleat. In the alternative, a container of floss may be mounted on one handle extension.

In another modification of this other, i.e., second embodiment of the flossing apparatus, a floss store is provided on one handle extension, anchored thereto. A loop is formed between the handles in a manner which will be hereinafter explained. The free end of the floss is then held and anchored on the aforementioned one extension while flossing is accomplished.

In a variation of this modification, the handle assembly accommodates an additional improvement. The other handle, which is now bare of cleats or the like, is provided with a bristle assembly at one end and, as a result, serves the dual function of a toothbrush and a flossing handle.

In yet another embodiment of the flossing apparatus, longer handles, i.e., handles which include extensions beyond the control segment of the floss loop are employed. The floss loop is continued to the free ends of the extensions where it passes through apertures thereon to form another loop. The result is a double floss loop or figure eight loop. This embodiment may be used advantageously with one hand; for example, by a handicapped flosser.

Other embodiments of the flossing apparatus invention are also disclosed, including another one-handed apparatus. They will, of course, be described hereinafter in some detail.

In a method of the invention related to flossing, the flossing handles are normally used by manipulating them separately to achieve any optimum working floss segment length and angular relationship between the handles for the particular flossing operation contemplated. Only a short length of the apparatus is inserted in the mouth. The flosser applies pressure to the control segment of the floss, to the handles or to both handles and control segment to control pressure on the tooth being flossed.

In another aspect of the invention, a method and apparatus are provided for performing laparoscopic surgery. One embodiment involves the use of two rods carrying a loop of flexible wire through a single operating passage in a laparoscope. Another embodiment involves the manipulation of two laparoscopic tubes separately inserted into a patient. Each tube has a wire extending through it which, when advanced past the distal end of the tube inside the patient, can be connected by suitable means so as to form a loop. In either embodiment, manipulation of the loop within the patient by manipulation of the rods through one tube (the one embodiment) or the manipulation of rods through two tubes (the other embodiment) facilitates using the working segment of the loop for any of numerous tasks such as electrodissection, fulguration, coagulation, cutting, cautery or the like.

In yet another aspect of the invention, a method and apparatus are provided for mechanical cutting or abrasion. A pair of working handles mount a wire or band in the form of a loop. The wire or band loop is moved by driving the wire or band in one direction, or reciprocating it. The working segment of wire or band changes constantly and acts as an abrasive element for polishing jewels, for example. On a larger scale the working segment can function as a "chain saw", in effect.

BRIEF DESCRIPTION OF THE DRAWING

The invention, including its construction and method of operation, as well as additional advantages thereof, is illustrated more or less diagrammatically in the drawings, in which:

FIG. 1 is a perspective view of a first form of flossing apparatus embodying features of the present invention;

FIG. 2 is another perspective view of the first form of flossing apparatus, illustrating the method of the invention employed in properly flossing with the apparatus;

FIG. 3A is a vector diagram illustrating certain features of the invention;

FIG. 3B is an illustration of the vector diagram of FIG. 3A on a three-axis (X, Y, Z) graph;

FIG. 4 is a view, similar to FIG. 1, illustrating a second form of flossing apparatus embodying features of the present invention;

FIG. 5 is a view, similar to FIG. 3, illustrating a modification of the second form of flossing apparatus;

FIG. 6 is a view, similar to FIG. 3, illustrating another modification of the second form of flossing apparatus;

FIG. 7 is a view, similar to FIG. 1, illustrating a third form of flossing apparatus embodying features of the present invention;

FIG. 8 is a perspective view of a variation on the flossing apparatuses shown in FIGS. 5, 6 and 7;

FIG. 9 is a perspective view of a variation on the flossing apparatuses shown in all preceding FIGURES;

FIG. 13 is a perspective view of another variation of the flossing apparatus shown in FIG. 5;

FIG. 14 is a perspective view illustrating a fourth form of flossing apparatus embodying features of the present invention;

FIG. 15 is a perspective view of a first form of laparoscopic surgery apparatus embodying features of the invention;

FIG. 16 is a perspective view of the rod and loop sub-assembly from the apparatus of FIG. 15;

FIG. 17 is a perspective view of another rod and loop subassembly for the apparatus of FIG. 15;

FIG. 18 is a perspective view of a second form of laparoscopic surgery apparatus embodying features of the invention;

FIG. 19 is an enlarged view of the working segment of loop in the second form of apparatus shown in FIG. 15;

FIG. 20 is a perspective view of a first form of mechanical sawing or abrasion apparatus embodying features of the invention; and FIG. 21 is a perspective view of a second for mechanical sawing or abrasion apparatus.

Figure 12:
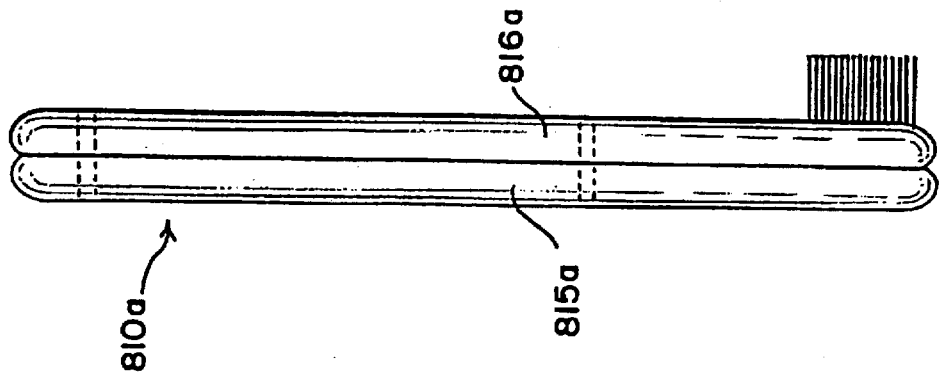
FIG. 12 is a perspective view of the FIG. 11 apparatus, further modified.

DESCRIPTION OF THE PREFERRED
EMBODIMENTS

Referring now to the drawings, and particularly to FIG. 1, a flossing apparatus embodying a first form of the present invention is seen generally at 10. The apparatus 10 comprises a pair of identical flossing handles 15 and 16 interconnected by a loop 17 of conventional dental floss.

The handles 15 and 16 are each about three inches long. Each is preferably formed of molded plastic, although wood, bamboo or any one of many different materials could be used. The handles 15 and 16 shown each have a circular cross-section, with a diameter of about one-quarter inch. The dimensions and shapes described are not critical to the invention, however, and may be varied without obvious limits.

Small apertures 20 and 21 are formed transversely through opposite ends of the handle 15. Identical apertures 30 and 31 are formed through corresponding opposite ends of the handle 16.

A piece of dental floss nine and one-half inches long is threaded through the apertures 21, 20, 30 and 31, and its free ends are tied together at a knot 35 to form the loop 17. With the apparatus 10 assembled in this way, the loop 17 is effectively divided into four segments, a floss working segment 36 between the apertures 20 and 30, a control segment 37 between the apertures 21 and 31, and a pair of side segments 38 and 39 paralleling corresponding handles 15 and 16.

The apparatus 10 is illustrated in FIG. 1 in its normal operating set-up. The handles 15 and 16 are inclined toward each other at the handle ends which carry the working segment 36 of the loop 17 between them. They are inclined in such a way that the working segment 36 is between one-quarter inch and one inch long. The opposite ends of the handles 15 and 16 have the control segment 37 of the loop 17 between them. The control segment 37 is then between about three and one-quarter inches and two and one-half inches long. In this operating set-up, the handles 15 and 16 would also normally be arranged so as to be non-coplanar.

Referring now to FIG. 2, the flossing apparatus 10 is shown in the hands RH and LH of the flosser as it is used according to the method of the invention. The handles 15 and 16 are grasped between the thumb T and forefinger FF of the right hand RH and the left hand LH, respectively. The third, or other finger TF of one or both hands is then placed over or under the control segment 37 of the floss loop 17.

The flosser then inserts the working segment 36 of the floss loop 17 into position in front of or behind a tooth, or around a tooth (as shown). The handles 15 and 16 can be disposed in any angular relationship to each other in order to place the working segment 36 in the most advantageous position for each flossing operation, and the operation performed by changing that angular relationship or while maintaining it. Flossing pressure is applied by the third, or other finger(s) TF of the flosser's hands pushing or pulling on the control segment 37 of the floss loop 17. In the alternative, this flossing pressure can also be maintained by tilting (pushing or pulling) the handles away from each other at the control segment.

In geometry terms, the vectors defined by the two handles 15 and 16 can be deployed in such fashion as to be linearly independent of each other. That is, the handles 15 and 16 can be deployed in space in such fashion that their vectors never meet, if extended; even when they are not parallel. The loop 17 that is formed by floss passing through the apertures in the handles can, in fact, be non-planar. This confers more degrees of freedom on the handles 15 and 16 and the loop segment 36 at the business end of the handles. This is very different from prior art flossing implements. They are not only coplanar, usually being configured in a "fork" geometry, but the plane of the floss segment and the plane of the arms or handles are normally coupled rigidly.

The mathematical expression of this relationship in the present invention illustrates the distinction between the present invention and the prior art. Referring now to the illustration of FIG. 3, consider one handle 15 to be a directed line segment called VECTOR, $\vec{V}_A$, where the other handle 16 is a directed line segment called VECTOR, $\vec{V}_B$. The working segment 36 of the floss is also a directed line segment called VECTOR, $\vec{V}_{WORKING}$, where the size of the segment can vary. The control segment 37 of the floss is not independent, since $\vec{V}_{CONTROL\ SEGMENT}$, is defined by the relation:

$$\vec{V}_{CONTROL\ SEGMENT} = \vec{V}_A - \vec{V}_B - \vec{V}_{WORKING\ SEGMENT}$$

(this, of course, is why the $\vec{V}_{WORKING\ SEGMENT}$ is determined by $\vec{V}_A$, $\vec{V}_B$ and $\vec{V}_{CONTROL\ SEGMENT}$. The coplanarity (linear dependence) relation is thus defined by $[\vec{V}_A \times \vec{V}_B] \bullet \vec{V}_{WORKING\ SEGMENT} = 0$, where the vector operators indicate VECTOR CROSS PRODUCT and VECTOR DOT PRODUCT, respectively. The NON-COPLANARITY CONDITION, which is a feature of the present invention, is defined by $[\vec{V}_A \times \vec{V}_B] \bullet \vec{V}_A$ working segment≠0.

Why is this relationship important? The object of using a tool to deploy floss segments within the mouth is to avoid having to distend the mouth unduly, or to trigger a gag reflex, or to insert non-hygienic fingers, or to insert fingers encased in latex, which has the disadvantage of tasting bad, smelling unpleasant and triggering allergic reactions to latex. This means that the floss segment should be deployable without having to change the orientation of the handles, point for point. The degrees of freedom inherent in the present invention allow the apparatus to move relatively little inside the mouth while permitting complete flexibility in deploying the working floss segment. There should be as little of the apparatus in the mouth as possible, aside from the floss segment.

In the present invention, the working floss segment is variable in length, as well as orientatable in space. The apparatus allows the working floss segment to be long or short, at will. It also allows the floss working segment to be taut, or slack, by itself, or pulled around a tooth or pushed against a tooth. That is, the floss working segment can be put under tension in either a line segment (when inserting between teeth) or in a curvilinear arc convex to the front of the mouth (when pushing against the tooth) or concave to the front of the mouth when pulling against a tooth.

Referring now to FIG. 4, a flossing apparatus embodying a second form of the present invention is seen generally at 110. The apparatus 110 is, in many respects, identical in construction to the flossing apparatus 10 hereinbefore discussed. To the extent that components are identical, corresponding reference numerals, plus one-hundred digits, are used.

As seen in FIG. 4 a floss loop 117 is mounted on a pair of identical flossing handles 115 and 116 by passing it through apertures 120 and 130 on corresponding ends of the handles and apertures 121 and 131 spaced about three inches from corresponding apertures 120 and 130. The loop 117 is knotted at 135 and includes a working segment 136, an operating segment 137 and side segments 138 and 139.

Unlike the apparatus 10, however, the handles 115 and 116 have handle extensions 155 and 156 below the apertures 121 and 131. These extensions 155 and 156 are each approximately four inches long, making the handles 115, 155 and 116, 156 each about seven inches long.

This configuration of the flossing apparatus 110 permits the flosser to grip the handle extensions 155 and 156 and manipulate the working segment 136 of the floss from a point further removed from the mouth. All of the advantages of the apparatus 10 are retained.

Referring now to FIG. 5, a modification of the second form of flossing apparatus is illustrated at 210. The apparatus 210 is, in most respects, identical to the flossing apparatus 110 hereinbefore discussed. To the extent that components are identical, corresponding reference numerals, plus one-hundred digits, are used.

As seen in FIG. 5, rather than being knotted at opposite free ends to form a loop, the loop 217 is formed by passing opposite ends 261 and 262 of the piece of floss through both apertures 221 and 231, in opposite directions. One end 261 is then wrapped numerous times around a cleat 271 on the handle extension 256 to form an anchored store of floss. The other end 262 is wrapped around a similar cleat 272 on the handle extension 255 to anchor it there.

By passing the opposite ends of the floss element through apertures 221 and 231 in this fashion, a "virtual loop" is formed. In other words, even though opposite ends 261 and 263 of the piece of floss are not tied together, a "virtual loop" is created. This permits the floss element to be manipulated by the handles in the same fashion as the embodiment of apparatus 110. In this arrangement, the "virtual loop" also behaves similarly to the embodiment of apparatus 110 in that, by manipulating the handles, the working segment 236 may be lengthened or shortened while correspondingly shortening or lengthening a pair of overlying control segments 237. As described in detail below, and in relation to other embodiments, this "virtual loop" feature of the invention in the present embodiment allows for the attachment of a thread storing device or other means to one or more of the handles.

The second form of flossing apparatus 210 is employed using the same method described with relation to the apparatus 110. As will be seen, however, it is not necessary to remove and replace the floss loop 217 after use. Floss is simply unwound from the store 261 on the cleat 271 for an inch or two and pulled through the apertures 231, 221, 220, 230, 231 and 221, in that order. The floss is then anchored again at the cleat 272, after which the excess can be cut off. This permits a very frugal use of floss since, for a single user, only one inch of new floss is needed for each "freshening". Alternatively, a completely pristine nine to ten inches of floss can be withdrawn for a new use and the excess discarded. An unused working segment 236 of floss is then in position.

Referring now to FIG. 6, another modification of the second form of flossing apparatus is illustrated at 310 (only the handle extensions 355 and 356, corresponding to the extensions 255 and 256 in FIG. 5, are shown). In the apparatus 310, a mounting receptacle 375 is affixed to the handle extension 356 and, in this receptacle, a standard small-size floss capsule 376 is removable mounted.

Floss is drawn from the capsule 376 and threaded through handle apertures in the manner illustrated in FIG. 5. When sufficient floss to reach and go well past an anchor cleat 372 on the handle extension 355 has been reached, the floss at the capsule 376 is placed under the conventional anchor cleat 371 associated with it. The free end is then anchored onto the cleat 372.

With regard to the aforedescribed modifications of the second embodiment, a wide variety of floss storage and anchoring mechanisms could be used. In addition, where such storage capability is provided, a floss cutting mechanism on the handle extension opposite the storage mechanism is preferably incorporated.

Referring now to FIG. 7, a flossing apparatus embodying a third form of the present invention is seen generally at 410. The apparatus 410 is, in many respects, identical in construction to the flossing apparatus 110 hereinbefore discussed. To the extent that components are identical, corresponding reference numerals, plus three-hundred digits, are used!

As seen in FIG. 7, the floss loop 417 is only part of a larger, double-loop 417, 418. The lower loop 418 is formed by crossing the ends of the length of floss through the apertures 421 and 431 and extending those ends downwardly along the handle extensions 455 and 456 to apertures 422 and 432 in corresponding extensions. The ends of the floss segment are then passed inwardly through the apertures 422 and 432 and tied together at a knot 445.

With this configuration apparatus 410, flossing can be done easily with one hand. The handle extensions 455 and 456 are gripped between fingers of one hand, somewhat like chopsticks, and the position, length and pressure applied by the floss working segment 436 controlled in this way.

Referring now to FIG. 8, a variation of the apparatuses 210, 310 and 410 hereinbefore discussed is seen in the flossing apparatus 510 (partially shown). It amounts to the creation of a spaced pair of apertures 521a, 521b and 531a, 531b in each of the handles 515 and 516. In forming the control segment 537 of the floss, the floss ends are threaded in opposite directions through the upper set of apertures 521a, 531a and the lower set 521b, 531b, respectively. Upper and lower floss control segments 537a and 537b are, thus, formed.

Referring now to FIG. 9, a variation of all the apparatuses hereinbefore discussed is seen in the flossing apparatus 610 (partially shown). It has slots 625 and 635 leading into corresponding apertures 620 and 630 through the handles 615 and 616. The slots 625 and 626 are duplicated adjacent corresponding other apertures through the handles (not shown) at their opposite ends. This slot construction permits preformed or pretied loops of floss 617 to be mounted on the handles by sliding them through corresponding slots into related apertures.

Figure 10:
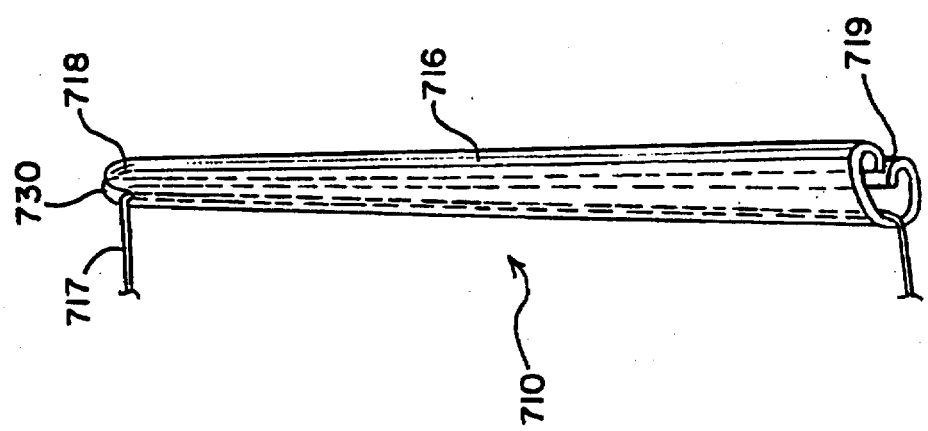
FIG. 10 is a perspective view of another variation of the flossing apparatuses shown.

Referring now to FIG. 10, another variation of apparatuses hereinbefore discussed is seen in the flossing apparatus 710 (partially shown). It comprises a pair of identical handles, but only one is shown, at 716. The handles are each formed with a bullet-shaped tip 718 at its working end. As seen at the opposite (lower) end in FIG. 10, each handle 716 is formed so that a slot 719 extends along its length, with inwardly curled edges 723 of the handle forming the slot. The slot 719 extends across the top of the tip 718 to form an aperture 730 in the tip for the floss 717. This construction also permits preformed or pretied loops of floss to be easily mounted and retained.

Figure 11:
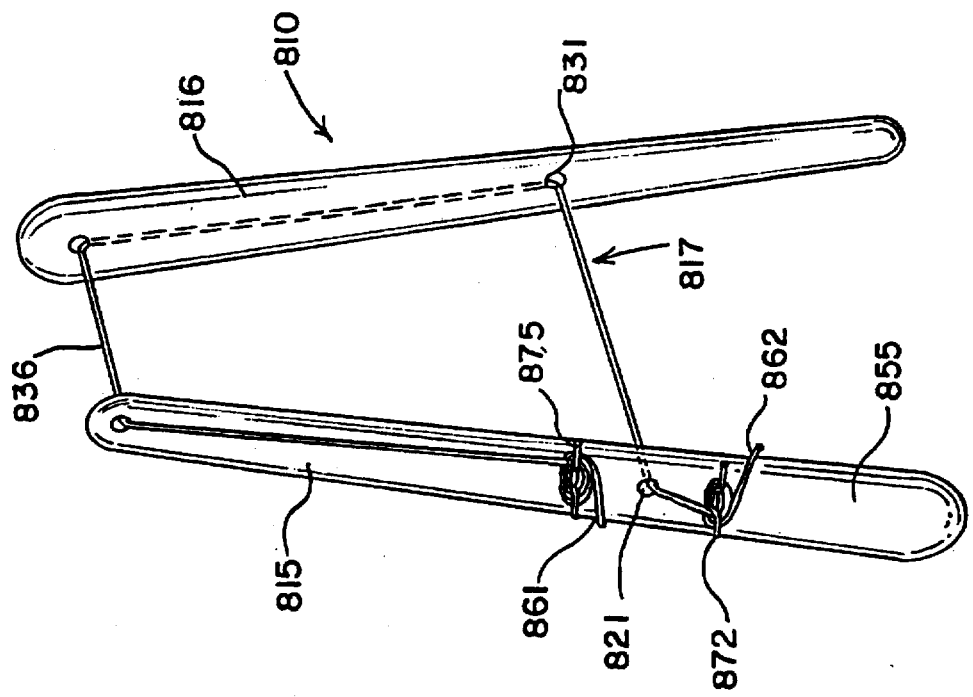
FIG. 11 is a perspective view of a variation of the flossing apparatus shown in FIG. 5.

Referring now to FIG. 11, yet another modification of the second form of flossing apparatus is illustrated at 810. The apparatus 810 is, in most respects, identical to the flossing apparatus 210 hereinbefore discussed. To the extent that components are identical corresponding reference numerals, plus six-hundred digits, are used.

As seen in FIG. 11, rather than being knotted at opposite free ends to form a loop, the loop 817 is formed by passing one end 862 of the piece of floss through both apertures 831 and 821, in that order. The end 862 is then wrapped numerous times around a transversely oriented cleat 872 on the handle extension 855 to form an anchored store of floss. The other end 861 of the piece of floss extends down along the flossing handle 815 to where it is anchored on another transversely oriented cleat 875.

In this form of the apparatus 810, the flosser is able to quickly adjust the length of the floss segment 836 while flossing. As new floss segments 836 are needed the flosser can quickly unwrap floss from the cleat 872, pull it through respective apertures from its free end 861, wrap the end 861 further around the cleat 875, and continue flossing without any delay.

The apparatus 810 also lends itself to further modification which results in a dual purpose apparatus; one which can also serve as a toothbrush. Such an apparatus is seen at 810a in FIG. 12.

FIG. 12 shows the apparatus 810a substantially identical to the apparatus 810 except that one handle can also function as a toothbrush. One gripping handle 816a has, on the end opposite its working floss segment end, a set 880a of bristles implanted to form a conventional brush, so that it can thus be used as a toothbrush.

Referring now to FIG. 13, still another modification of the second form of floss apparatus is illustrated at 1410. The apparatus 1410 is, in many respects, identical to the flossing apparatuses 710 and 810 hereinbefore discussed. As such, only portions of it are shown.

In the apparatus 1410, a virtual loop 1417 has free ends 1461 and 1462. The ends are threaded through apertures (not shown) in the handles 1415 and 1416. The free end 1462 is then wrapped numerous times around a rotatable spindle (not shown) within a storage drum 1480 fixed to the handle 1416.

The storage drum 1480 has a spindle latching button 1481 extending from it. The button 1481 is spring loaded outwardly into latching engagement with the spindle, thus normally preventing the spindle from rotating and allowing floss to be withdrawn. When the button 1481 is pressed, floss can be pulled from the drum.

Floss is drawn from the drum 1480 by pulling on the other end 1461 of the loop 1417. The floss is pulled through a brake block 1485 which has a one-way brake 1486 of conventional construction in it. The brake 1486 permits floss to pass through the brake block 1485 in one direction (down in FIG. 13), but prevents it from moving back through the block.

As will be seen, replacement floss in the loop 1417 can readily be made available for flossing by depressing the button 1481 and pulling the floss end 1461 through the brake block 1485. The end 1461 is then cut off on a conventional cutting element 1486 fastened to the handle 1415.

Referring now to FIG. 14, a third form of flossing apparatus embodying features of the invention is illustrated at 1510. The apparatus 1510 is designed to be operated with one hand H.

As illustrated, the apparatus includes a hollow handle 1515 which has a thumb shaped housing 1580, at one end, into which the user's thumb T is inserted. Another hollow handle 1516 has a middle finger-tip shaped housing 1581, at a corresponding end, into which the user's middle finger tip F is inserted.

A loop 1517 of floss interconnects the handles 1515 and 1516. The loop passes through apertures 1520 and 1521 in the handle 1515, and also through apertures 1530 and 1531 in the handle 1516. In doing so it passes through the hollow handles, as will be seen.

The loop 1517 is actually a length of floss which is threaded through the handles in the aforedescribed manner and, then, tied together by a knot 1535 at its opposite free ends. In this arrangement the loop 1517 formed has a working segment 1536 of floss between the free ends of the handles 1515 and 1516 and a control segment 1537 between its thumb and finger-tip housings 1580 and 1581.

Manipulation of the working floss segment 1536 is accomplished by manipulating the handles with the thumb and middle finger. At the same time the control segment 1537 is manipulated by the free index finger. The flossing operation advantages achieved with the previously described embodiments are also achieved with this one-handed embodiment.

Referring now to FIGS. 15 and 16, a laparoscopic surgery apparatus embodying features of one form another aspect of the invention is seen generally at 910. The apparatus 910 includes a conventional 12 mm O.D. laparoscope 911 containing an 8 mm I.D. channel 912 through which an operating assembly 913 extends.

The operating assembly 913 includes two hollow rods, 915 and 916, i.e., rods with corresponding passages 920 and 921 extending through them, from end to end. A flexible wire 925 extends through each of said passages and has its free ends tied together at 935 to form a loop 937.

The loop 937 includes a working segment 938 between adjacent one ends of the passages 920 and 921 and a control segment 939 between the opposite ends. With the operating assembly 913 in place in the laparoscope 911, and the scope inserted into a patient and properly positioned for surgery, the working segment 938 can be manipulated in 3-dimensions by manipulating the rods 915 and 916 from outside the patient's body while also manipulating the control segment 939 of the loop 937.

The working segment 938 can, accordingly, be used to position a device (e.g., a chemical or radioactive bead), or act as a ligature or, even carry an electrical current to a selected location. A ligature can be formed by wrapping the working segment 938 around an object inside the patient's body cavity. Used as an electrical current conductor the working segment can be used in electrodissection, fulguration, etc., without the danger of grounding through unanticipated contact with an internal organ.

In use, the loop 937 of the operating assembly is manipulated like the flossing devices hereinbefore described, albeit on a more restricted basis. The constraint of the laparoscope channel I.D. is felt in manipulating the working segment 938, of course. Nevertheless, most of the advantages of positioning and control of the working segment 938 which are achieved are identical to those hereinbefore ascribed to the flossing apparatuses.

Another form of laparoscopic surgery apparatus embodying features of the invention is seen in FIG. 17 at 1210. The apparatus includes a conventional laparoscope 1211 through which an operating assembly 1213 extends.

The operating assembly 1213 is very similar in design to the flossing apparatus 1510 shown in FIG. 14. Two hollow rods 1215 and 1216 have passages extending through them. The rod 1215 has an open free end 1220 and an aperture 1221 adjacent its thumb held end. The rod 2516 has an open free end 1230 and an aperture 1231 adjacent its middle finger-tip held end.

A flexible wire 1225 extends through the handle passages to form a loop having a working segment 1238 and a control segment 1239. With the operating assembly 1213 in place in the laparoscope 1211, and the scope inserted with one hand into a patient and properly positioned for surgery, the working segment 1238 can be manipulated in three-dimensions with two fingers and the thumb on one hand.

Referring now to FIGS. 18 and 19, a laparoscopic surgery apparatus embodying features of another embodiment of the invention is seen generally at 1010. The apparatus 1010 includes two identical sleeves 1011 and 1012 of convention steel construction. The stainless sleeves have corresponding channels 1015 and 1016 extending through them and puncture points 1020 and 1021 formed at one end.

A flexible wire 1025 having hooked free ends 1026 and 1027 is threaded through the channels 1015 and 1016 into the patient's body cavity after the sleeves 1011 and 1012 have been inserted by puncture in the manner shown in FIG. 15. The free ends 1026 and 1027 of the wire 1025 are then connected by hooking them in the manner illustrated or by some other suitable technique; for example by magnetic coupling. A loop 1037 is thus formed extending into and out of the patient through the sleeves 1011 and 1012.

The loop 1037, like those previously discussed in other contexts, now has a working segment 1038 between adjacent puncture points 1020 and 1021 within the body cavity and a control segment 1039 between opposite ends outside the patient's body. The working segment 1038 can be manipulated in 3-dimensions by manipulating the sleeves 1011 and 1012 from outside the patient's body while also manipulating the control segment 1039 of the loop 1037. In use, the apparatus 1010 is manipulated in a manner apparent from descriptions of previous embodiments.

Now referring to FIG. 20, the invention is shown in yet another embodiment, an apparatus 1110 for mechanical cutting or abrasion. The apparatus 1110 comprises a pair of handles 1115 and 1116 interconnected by a loop or band 1117 of wire.

The handles 1115 and 1116 may be formed of stainless steel, for example. Each is about six inches long. Small apertures 1120 and 1121 are formed transversely through opposite ends of the handle 1115. Identical apertures 1130 and 1131 are formed through corresponding opposite ends of the handle 1116.

A length of high strength, alloy wire is threaded through the apertures 1120, 1130, 1131 and 1121, in that order. The free ends of the wire are then connected to a conventional, battery operated drive capstan 1132 fastened to the handle 1115.

A working segment 1138 of wire is then disposed between the aperture 1120 and 1130. The capstan 1132 can be operated to reciprocate that segment 1138 or to move it continuously in one direction (with a sufficient length of wire, or an endless wire). The working segment 1138 can be manipulated in space, in a manner hereinbefore made clear, to polish or cut a work piece; a jewel, for example.

On a larger scale the apparatus 1110 can function as a saw, i.e., in a "chain saw" operation. For example, the band 1117 of wire can be separable in its working segment 1138 and reconnected around a log. The mode of operation will be apparent from the foregoing description of other embodiments of the invention.

Referring now to FIG. 21, another form of apparatus for cutting or abrading is illustrated at 1310. The apparatus 1310 may be compared in structure and function to the apparatus 1110 seen in FIG. 20, except that its wire loop 1317 is a virtual loop rather than a real loop.

More specifically, the apparatus 1310 includes handles 1315 and 1316 having apertures 1320, 1321 and 1330, 1331 in them, respectively. A length of cutting or abrading wire is threaded through these apertures, as illustrated, and its opposite ends 1361 and 1362 are fastened to corresponding cleats 1371 and 1372 on the handles 1316 and 1315, respectively. In this regard the loop 1317 configuration is similar to that shown in FIG. 5.

The loop 1317 includes a working portion 1336 between the apertures 1320 and 1330 and segments 1338 and 1339 which extend along the sides of respective handles. These side segments 1338 and 1339 are routed over control rollers 1381 and 1382, the rollers being mounted on corresponding free ends of control members 1383 and 1384, respectively. The opposite end of each control member is pivotally connected to the end of a corresponding handle 1315 and 1316, as at 1391 and 1392.

Disposed between the handle 1315 and the control member 1384 is a coil spring 1395 of conventional construction. The coil spring 1395 is under compression and, as such, tends to urge the roller 1382 away from the handle 1315 and the roller 1381 towards the handle 1316.

In use in an abrading operation, for example, the operator grips the handles 1315 and 1316 near the pivots 1391 and 1392 of the control members. The working segment 1336 of the loop is ideally positioned on a work surface by arranging the handles 1315 and 1316 in space, constrained only by the loop 1317. The control member 1383 is then rhythmically pivoted away from and toward the handle 1316 with the fingers on one hand. The control member 1384 follows as the spring 1395 compresses and expands. The working segment 1336 moves back and forth through the apertures 1320 and 1330 and abrades the work piece as it does so.

While preferred embodiments of the invention have been described, it should be understood that the invention is not so limited and modifications may be made without departing from the invention. The scope of the invention is defined by the appended claims, and all devices that come within the meaning of the claims, either literally or by equivalence, are intended to be embraced therein.

We claim:

1. An apparatus comprising:
  a) first and second elongated handles, each of said handles having at least an upper and a lower aperture defined therethrough;
  b) a flexible element having an overall length and opposite ends, said flexible element extending through, and freely slidable through, each of said apertures in each of said handles;
  c) said flexible element forming at least one working segment of said element extending between said upper aperture of said first handle and said upper aperture of said second handle, and at least one control segment extending between said lower aperture of said first handle and said lower aperture of said second handle;
  d) said element extending substantially externally to said handles between said upper aperture and said lower aperture on each handle; and
  e) said handles being free to be moved in space relative to each other, except as constrained by said working segment and said control segment, whereby said working segment can be positioned, and the relative lengths of said working segment and said control segment can be varied, by manipulation of said handles and said control segment.

2. The apparatus of claim 1 wherein:
  f) said working segment has a first length defined by the distance between said upper apertures of said handles when said working segment is tensioned between said apertures;
  g) said control segment has a second length defined by the distance between said lower apertures of said handles when said control segment is tensioned between said apertures; and
  h) the sum of said lengths remaining substantially constant regardless of the positions of said handles when both of said segments are tensioned.

3. The apparatus of claim 2 wherein:
  i) the application of tension to said control segment along the first length of said control segment in any direction varies the first length of said working segment.

4. The apparatus of claim 1 wherein:
  f) said loop is a virtual loop formed by said opposite ends of said flexible element being fastened to said handles.

5. The apparatus of claim 2 wherein:
  i) said flexible element is threaded through said apertures to form a virtual loop between said handles.

6. The apparatus of claim 5 wherein said virtual loop further comprises:

j) a first attachment structure on said first handle for fixedly retaining one of said ends of said element;

k) a second attachment structure on said second handle for fixedly retaining the other of said ends of said element; and l) said element passing sequentially from said first attachment structure, through said lower aperture of said first handle, said lower aperture of said second handle, said upper aperture of said second handle and said upper aperture of said first handle, before attachment to said second attachment structure.

7. The apparatus of claim 1 wherein:

f) each of said opposite ends is fastened to the same handle.

8. The apparatus of claim 7 wherein:

g) said flexible element is a length of dental floss;

h) one of said opposite ends being wrapped around a storage device to form a store of floss;

i) the other of said opposite ends being held in a holding device.

9. The apparatus of claim 8 wherein:

j) said storage device includes means for selectively releasing floss from said storage device.

10. The apparatus of claim 8 wherein:

j) said storing and holding devices each comprise a holding cleat fastened to and extending transversely of said same handle.

11. The apparatus of claim 8 further comprising:

j) a brush element mounted on the other of said handles from said same handle.

12. The apparatus of claim 1 wherein:

g) said flexible element is a length of abrading material;

h) said apparatus further including mechanical means for moving a working segment of said loop relative to said handles to abrade a work-piece.

13. The apparatus of claim 2 wherein:

f) said flexible element is a length of abrading material;

g) said apparatus further including mechanical means for moving a working segment of said loop relative to said handles to abrade a work-piece.

14. An apparatus comprising:

a) first and second elongated handles, each of said handles having at least an upper and a set of lower apertures defined therethrough;

b) a first attachment structure on said first handle;

c) a second attachment structure on said second handle; and d) a flexible element having an overall length and opposite ends, one of said ends of said flexible element being fixedly attached at said first attachment structure to said first handle, said element passing sequentially from said first attachment structure through a lower aperture of said first handle, a lower aperture of said second handle, said upper aperture of said second handle, said upper aperture of said first handle, back through a lower aperture of said first handle and lower aperture of said second handle, the other of said ends being attached at said second attachment structure;

wherein the configuration of said element provides at least a working segment of said element extending between said upper apertures of said first and said second handles and at least one control segment of said element extending between said set of lower apertures of said first and said second handles.

15. The apparatus of claim 14 wherein said element is freely slidable within each of said apertures to provide a virtual loop to permit movement of said handles relative to each other to vary the lengths of said control segment and said working segment without varying the overall length of said element.

16. The apparatus of claim 15 wherein said set of lower apertures further comprises a first lower aperture and a second lower aperture on each of said first and second handles, said element extending from said first attachment structure through said second lower aperture of said first handle, said second lower aperture of said second handle, said upper aperture of said second handle, said upper aperture of said first handle, said first lower aperture of said first handle, and said first lower aperture of said second handle.

17. The apparatus of claim 16 wherein at least one of said first and second attachment structures further comprises a store to hold a portion of said element.

18. The apparatus of claim 17 wherein at least one of said first and second attachment structures further comprises a cleat to hold a portion of said element.

19. An apparatus comprising:

a) first and second elongated handles, each of said handles defining an upper aperture and a lower aperture;

b) a flexible element having opposite ends, said element passing through said apertures, one of said opposite ends extending from one of said lower apertures, the other of said opposite ends extending from the other of said lower apertures; and c) a clasping device mounted adjacent to each of said ends.

20. The apparatus of claim 19 wherein said clasping device further comprises a hook mounted adjacent to each of said ends.

21. The apparatus of claim 20 wherein said flexible element comprises a length of dental floss.

22. The apparatus of claim 20 wherein each of said handles further comprises a hollow sleeve defining said upper and lower apertures.

23. A method of positioning and moving a flexible element having an overall length and opposite ends, said method comprising:

a) providing first and second elongated handles, each of said handles defining an upper and a lower aperture;

b) providing a loop of flexible element, said loop formed by passing a length of said element through each of said apertures and allowing said length to freely slide therein, the portion of said element extending between the upper apertures of said first and said second handles defining a working segment, and the portion of said element extending between the lower apertures of said first and said second handles defining a control segment, said portions of said element extending between said upper and lower apertures of said first handle and the upper and lower apertures of said second handle extend substantially externally to said handles; and c) gripping said first handle in the fingers of one hand and the second handle in the fingers of the other hand to tension and position said working segment.

24. The method as recited in claim 23 further comprising the steps of:

d) exerting outwardly directed pressure with the fingers on said control segment and on the handles to further tension said working segment; and e) manipulating the handles independently relative to each other except for any constraint imposed by the length of said loop so as to permit substantially unlimited orientation and control of said working segment.

25. A method of positioning and moving a flexible element within a cavity, said method comprising:
   a) providing a flexible element having two ends, each of said ends having a hook fastened to said end for forming a loop in said flexible element upon connection of said hooks to each other;
   b) providing a pair of elongated hollow sleeves, each of said sleeves defining an upper and a lower aperture, said flexible element extending through said apertures and through said sleeves;
   c) inserting a portion of said sleeves into a cavity;
   d) attaching said hooks to each other within said cavity; and
   e) manipulating said sleeves and said element to maneuver said working element within said cavity.

26. The method of claim 25 wherein said element further comprises a length of dental floss.

27. A device for performing laparoscopic surgery, comprising:
   a) a laparoscope having a channel of predetermined diameter therethrough; and
   b) an apparatus for positioning and moving a flexible element within a body cavity extending through said channel;
   c) said apparatus comprising first and second elongated handles;
   d) an elongated, flexible element having opposite ends; and
   e) each of said elongated handles having passage means therethrough for receiving said flexible element;
   f) said flexible element extending through said passage means in each handle and forming a loop between said handles;
   g) said flexible element being free to move in said passage means;
   h) said loop including a working segment of flexible element extending between said handles adjacent corresponding one ends of said handles;
   i) said handles being free to be moved in space relative to each in any way, except as constrained by said loop, whereby said working segment can be positioned and moved by manipulation of said handles and said loop.

28. A method of performing laparoscopic surgery on a patient, said method comprising:
   a) providing a pair of elongated hollow sleeves, each of said sleeves defining an upper and a lower aperture;
   b) inserting said sleeves into separate incisions in said patient;
   c) inserting a flexible element having hooked free ends into said sleeves;
   d) hooking said free ends of said element to each other within said patient to form a loop having a working segment of said element between said sleeves within said patient and a control segment between said sleeves outside of said patient; and
   e) manipulating said sleeves and said control segment to maneuver said working segment within said patient.

* * * * *